United States Patent
Terwey et al.

(10) Patent No.: US 9,585,643 B2
(45) Date of Patent: Mar. 7, 2017

(54) CARRIER TUBES FOR CLOSURE DEVICES

(75) Inventors: Russell D. Terwey, St. Michael, MN (US); Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 425 days.

(21) Appl. No.: 13/590,338

(22) Filed: Aug. 21, 2012

(65) Prior Publication Data

US 2014/0058438 A1     Feb. 27, 2014

(51) Int. Cl.
    *A61B 17/10*     (2006.01)
    *A61B 17/00*     (2006.01)
    *A61B 17/34*     (2006.01)

(52) U.S. Cl.
    CPC ...... *A61B 17/0057* (2013.01); *A61B 2017/00623* (2013.01); *A61B 2017/00654* (2013.01); *A61B 2017/00659* (2013.01); *A61B 2017/3454* (2013.01)

(58) Field of Classification Search
    CPC ................................ A61B 17/08; A61B 17/10
    USPC ....... 606/108, 139, 142, 151, 191, 194, 198, 606/213
    See application file for complete search history.

(56) References Cited

U.S. PATENT DOCUMENTS

| | | | |
|---|---|---|---|
| 5,895,410 A * | 4/1999 | Forber ............ | A61B 17/12022 606/191 |
| 6,045,569 A | 4/2000 | Kensey et al. | |
| 6,090,130 A | 7/2000 | Nash et al. | |
| 6,132,450 A * | 10/2000 | Hanson ................. | A61F 2/0095 604/96.01 |
| 6,321,450 B1 * | 11/2001 | Semenov et al. ......... | 29/890.01 |
| 7,144,393 B2 * | 12/2006 | DiPoto et al. .................... | 606/1 |
| 7,172,620 B2 * | 2/2007 | Gilson ............ | A61B 17/12031 606/108 |
| 7,201,725 B1 * | 4/2007 | Cragg .................. | A61B 5/1076 600/587 |
| 7,618,436 B2 | 11/2009 | Forsberg | |
| 7,749,248 B2 | 7/2010 | White et al. | |
| 7,837,705 B2 | 11/2010 | White et al. | |
| 7,931,670 B2 | 4/2011 | Fiehler et al. | |
| 7,955,353 B1 | 6/2011 | Ashby et al. | |

(Continued)

FOREIGN PATENT DOCUMENTS

WO         9639945 A1    12/1996

OTHER PUBLICATIONS

PCT International Search Report for PCT International Application No. PCT/US2013/051068, mailed Jan. 13, 2014 (pp. 5).

*Primary Examiner* — Vy Bui
(74) *Attorney, Agent, or Firm* — Holland & Hart

(57) ABSTRACT

A deployment device having a carrier tube, for bringing a sealing plug into position within a puncture tract or incision and deploying the sealing plug within the incision or puncture tract, towards the outer surface of a tissue puncture, is provided. The carrier tube is designed to facilitate easier deployment and improved compaction of the sealing plug, the sealing plug often made of collagen. The carrier tube is adapted to prevent the premature hydration of the sealing plug, where premature hydration of the sealing plug may result in difficulty in deploying the sealing plug. The carrier tube is designed to facilitate easier loading of puncture tract closing elements into the distal end of the carrier tube.

20 Claims, 15 Drawing Sheets

(56) References Cited

U.S. PATENT DOCUMENTS

| | | | |
|---|---|---|---|
| 8,359,721 B2* | 1/2013 | Melsheimer | A61F 2/95 29/235 |
| 2003/0153927 A1 | 8/2003 | DiPoto et al. | |
| 2006/0178739 A1* | 8/2006 | Shalaby | A61F 2/90 623/1.49 |
| 2010/0324585 A1 | 12/2010 | Miles et al. | |

* cited by examiner

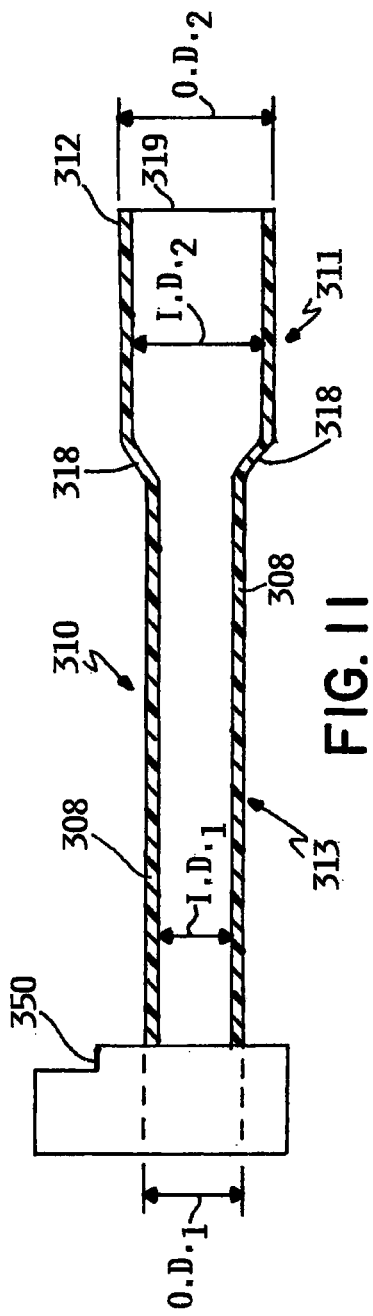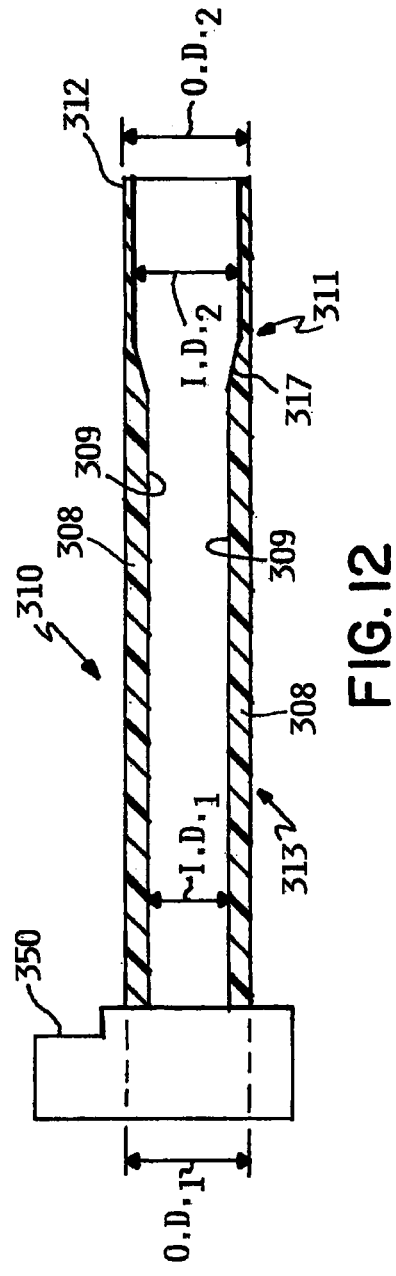

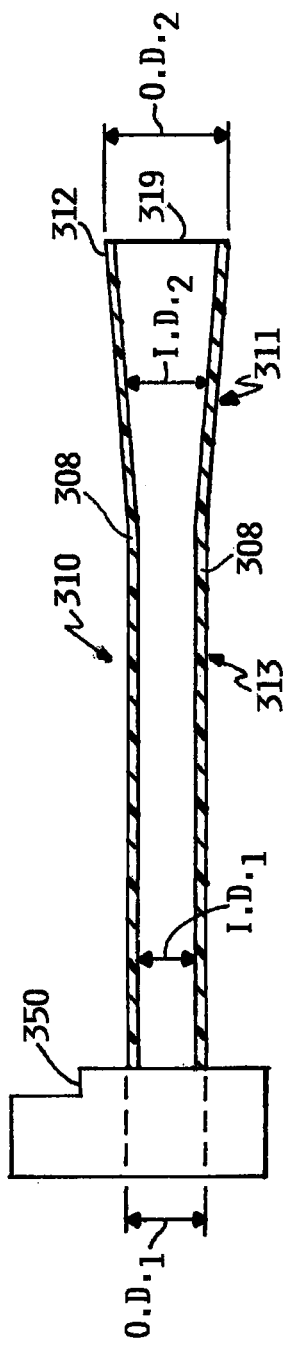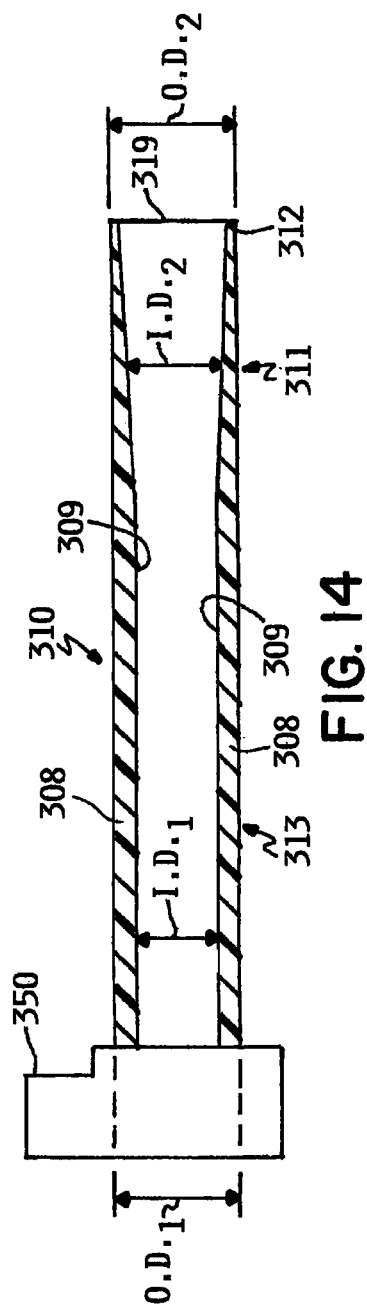

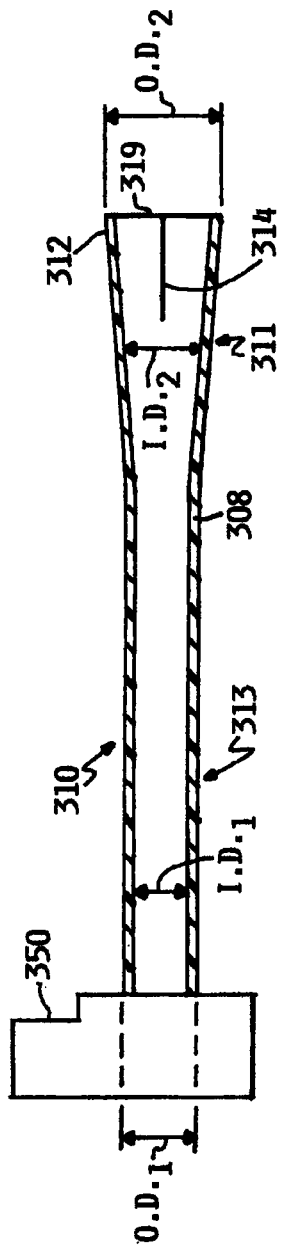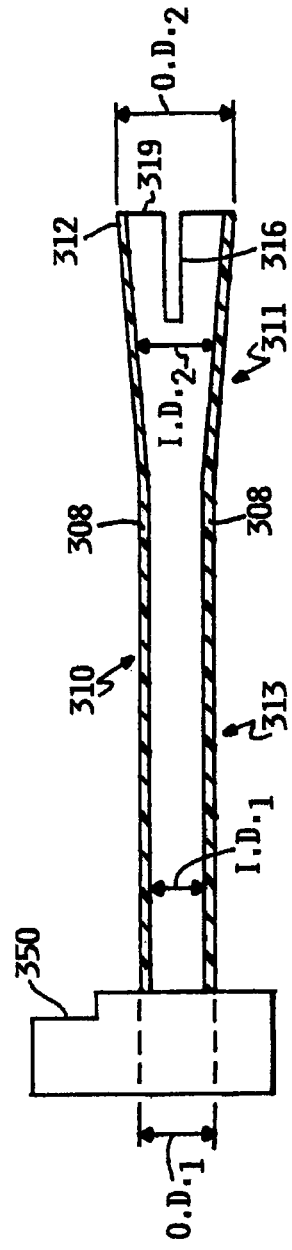
FIG. 19
FIG. 20

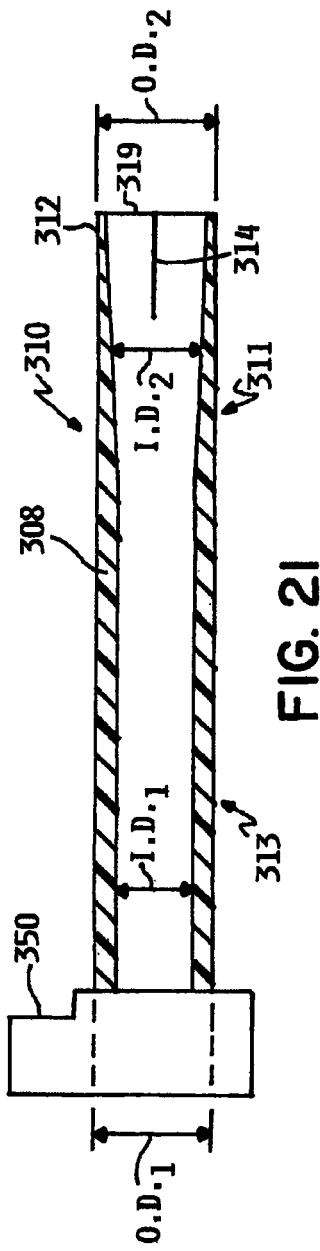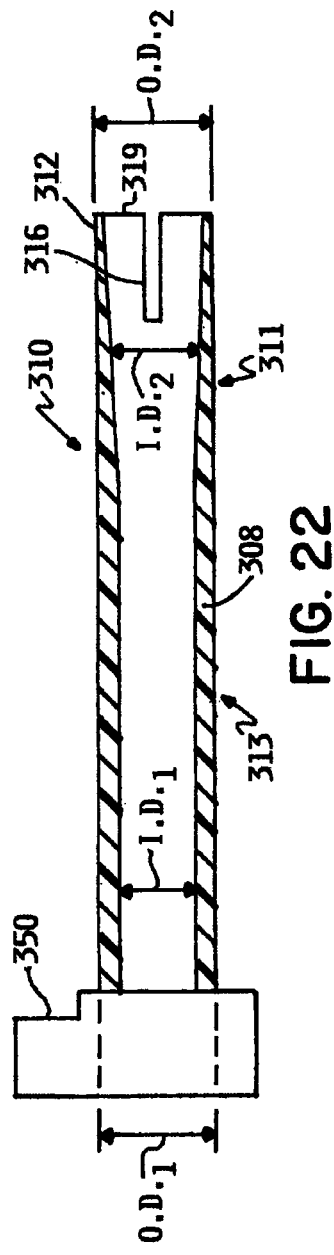

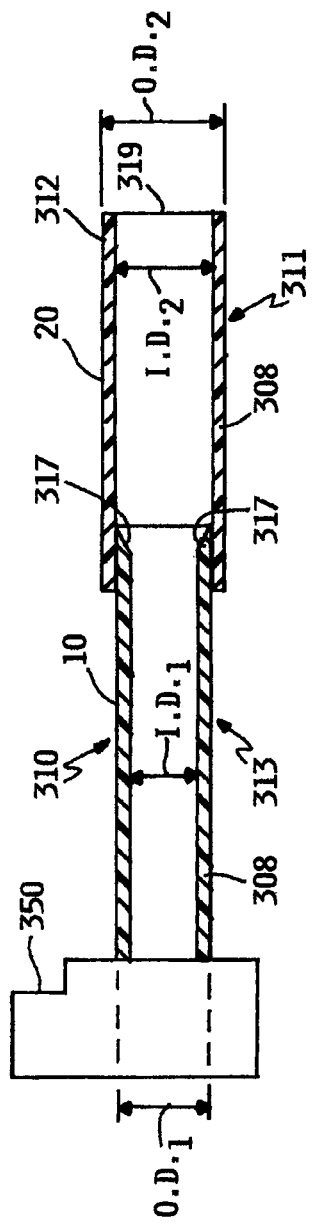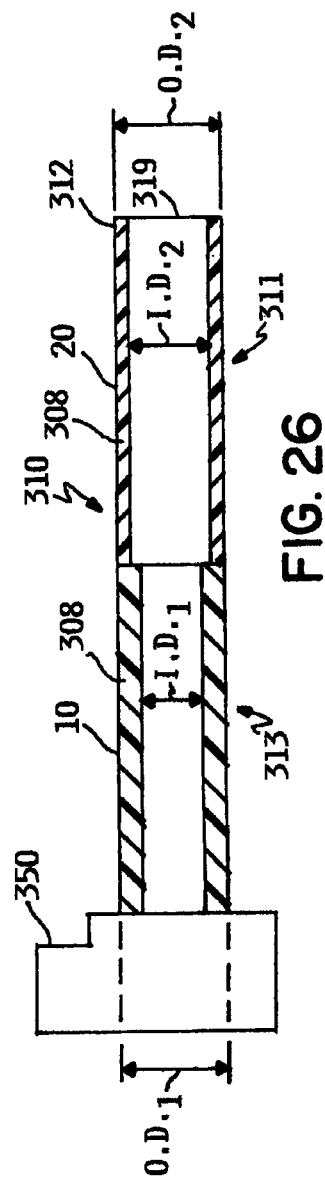

CARRIER TUBES FOR CLOSURE DEVICES

FIELD OF THE INVENTION

This invention relates generally to medical devices and more particularly to tools for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,045,569; 6,090,130; 7,618,436; 7,749,248; 7,837,705; 7,931,670, and related patents and patent applications, all of which are hereby incorporated by reference.

Typical closure tools or devices such as the ones described in the above-mentioned patents and patent applications place a sealing plug at one side of the tissue puncture site and an anchor on the other side of the tissue puncture site. Successful deployment of the sealing plug requires that it be ejected from within a device sheath or carrier tube into the incision or puncture tract and tamped down to an outer surface of the tissue puncture using a tamping tube (also called a compaction tube). The carrier tube extends from the proximal end to the distal end of the closure tool and includes an outlet at the distal end. The carrier tube can be made of plastic or other material and is designed for insertion through a sheath, and the sheath is designed for insertion through a percutaneous incision in a tissue layer and into a lumen. The sealing plug is initially disposed within the carrier tube, prior to deployment, and the anchor is positioned axially along the carrier tube. When the carrier tube is pulled away from the sealing plug and anchor, after the anchor has been positioned, for example, in a lumen, the sealing plug is deployed into the puncture tract. The carrier tube also houses a tamping device within, and the tamping device advances the sealing plug towards the anchor.

In a manually operated tool, the tamping procedure cannot commence until the carrier tube (within which the tamping device, such as a tamping tube, is located) has been removed so as to expose the tamping tube for manual grasping. The tamping tube is manually grasped and tamped against the sealing plug, setting the sealing plug within the incision or puncture tract, against an outer surface of the tissue puncture. In an automatic tamping system, the closure tool can have an automatic driving mechanism for automatically tamping the sealing plug within the incision or puncture tract toward the outer surface of the tissue puncture. The closure tool can have a tamping tube or tamping rack disposed adjacent to the sealing plug, such that the tamping tube or rack is driven by the automatic driving mechanism to tamp the sealing plug into the desired placement.

Under certain conditions, the sealing plug may need to be ejected from the carrier tube earlier than is usual or expected. In addition, the sealing plug may react with bodily fluids prior to deployment and, thus, make deployment not as easy as expected. Further, easier, more efficient, loading of the sealant plug and knot into the carrier tube would assist in decreasing manufacturing cycle time, and hence boost manufacturing efficiency and productivity. Accordingly, there is a need for improving the mechanism for deployment of the sealing plug at the site of a tissue puncture or incision, and improving manufacturing cycle time for the loaded carrier tube.

SUMMARY

In one of the many possible embodiments, the present invention relates to a tissue puncture closure device for partial insertion into and sealing of a tissue wall puncture. The tissue puncture closure device includes a carrier tube, a suture, an anchor, and a sealing plug. The suture extends from a first end of the closure device to a second end of the closure device. The anchor is insertable through the tissue wall puncture and is attached to the suture at the second end of the closure device. The sealing plug is slidingly attached to the suture, proximal the anchor, and is carried in the carrier tube in a pre-deployment position. The carrier tube brings the sealing plug into position within the puncture tract or incision, and deploys the sealing plug within the incision or puncture tract, towards the outer surface of the tissue puncture, on the proximal side of the internal tissue wall. The suture forms a self-tightening slip-knot on the proximal side of the sealing plug and, when the carrier tube is pulled away from the anchor, the suture cinches the anchor and the sealing plug together, sandwiching the tissue wall between the anchor and the sealing plug.

The carrier tube can be designed to facilitate easier deployment of the sealing plug, the sealing plug being made of a biocompatible resorbable material, for example, collagen. The carrier tube can be adapted to prevent the premature hydration of the sealing plug, where premature hydration of the sealing plug may result in difficulty in deploying the sealing plug. The carrier tube can also be designed to allow some hydration or lubrication of the sealing plug in the carrier tube, to facilitate easy deployment of the sealing plug. The need to facilitate hydration of the sealing plug in the carrier tube or prevent early hydration of the sealing plug in the carrier tube can be dependent upon the nature and characteristics of the material of the sealing plug. The carrier tube can also be designed to facilitate easier loading of the sealing plug and knot into the carrier tube, without significant increase in the distal end profile of the carrier tube.

According to one aspect of the invention, the carrier tube comprises a tubular member wherein the distal end of the tubular member includes a broadened tubular structure, such that the inner diameter of the proximal portion of the carrier tube is smaller than the inner diameter of the distal portion of the carrier tube, and the outer diameter of the proximal portion of the carrier tube is smaller than the outer diameter of the distal portion of the carrier tube.

In another aspect of the invention, the carrier tube comprises a tubular member wherein the distal portion of the carrier tube includes at least one slit and/or at least one slot. In yet another aspect of the invention, the carrier tube comprises a tubular member wherein the distal portion of the tubular member includes a broadened tubular structure, such that the inner diameter of the proximal portion of the carrier tube is smaller than the inner diameter of the distal portion of the carrier tube, and the outer diameter of the proximal portion of the carrier tube is smaller than the outer diameter of the distal portion of the carrier tube. The inner diameter of the carrier tube can gradually increase from the proximal portion of the carrier tube to the distal portion of the carrier tube, and the outer diameter of carrier tube can gradually increase from the proximal portion of the carrier tube to the distal portion of the carrier tube. The carrier tube can, alternatively, also include at least one slit and/or at least one slot.

According to yet another aspect of the invention, the carrier tube comprises a proximal portion and a distal portion. The walls of the distal portion of the carrier tube are somewhat thinner than the walls of the proximal portion of the carrier tube. The distal portion of the carrier tube also has an inner diameter greater than the inner diameter of the proximal portion of the carrier tube, and the outer diameter of the proximal portion of the carrier tube is substantially similar or the same as compared to the outer diameter of the distal portion of the carrier tube. Thus, the exterior profile of the distal portion of the carrier tube is not greatly different as compared to the exterior profile of the proximal portion of the carrier tube, although the inner diameter of the distal portion of the carrier tube is greater than the inner diameter of the proximal portion of the carrier tube. Alternatively, the distal end of the carrier tube can also include at least one slit and/or at least one slot.

According to yet another aspect of the invention, the carrier tube comprises a proximal portion and a distal portion. The distal portion of the carrier tube has an inner diameter greater than the inner diameter of the proximal portion of the carrier tube. Further, the distal end of the carrier tube includes a slit wherein the edges of the slit overlap.

In yet another aspect of the invention, the carrier tube comprises two tubular members which are fixed together, forming a continuous lumen therethrough. The inner diameter of the tubular member forming the distal portion of the carrier tube is greater than the inner diameter of the tubular member forming the proximal portion of the carrier tube. The distal end of the carrier tube can, alternatively, include at least one slit or slot.

A further aspect of the present invention relates to a method of sealing a puncture in a tissue wall or in a vessel, wherein the puncture is accessible through a percutaneous incision. The method can include providing a tissue puncture closure device including a carrier tube having a sealing plug, and a suture forming a self-tightening slip-knot on the proximal side of the sealing plug, loaded in the distal end of the carrier tube, and an anchor nested along the carrier tube. The method includes inserting the anchor through the tissue puncture and, for example, into the vessel, positioning the sealing plug within the puncture tract in a pre-deployment position, and deploying the sealing plug from the carrier tube, adjacent to the outer surface of the vessel. The sealing plug can be partially hydrated before deployment to assist in proper positioning, easier deployment, and good puncture tract compaction of the sealing plug. Alternatively, dependent at least to some extent on the sealing plug material, the unwanted early hydration of the sealing plug can be avoided based on the structure of the carrier tube, thus assisting in the proper positioning of the sealing plug in the puncture tract.

The method can also include providing an insertion sheath and a carrier tube, the sealing plug positioned in the carrier tube in a pre-deployment position. The method can include inserting the insertion sheath into the puncture tract, inserting the carrier tube, including the end loaded sealing plug and self-tightening suture slip-knot, through the insertion sheath into the puncture tract, inserting the anchor to the vessel lumen, and deploying the sealing plug in the puncture tract, adjacent the outside of the vessel. The sealing plug can be partially hydrated prior to deployment, to assist in proper positioning of the sealing plug in the puncture tract and assist in easier deployment of the sealing plug. Alternatively, the structure of the carrier tube can assist in the prevention of early hydration of the sealing plug, desired as a result of the particular material composing the sealing plug, and thus assist in proper positioning of the sealing plug in the puncture tract after deployment. The method can include cinching the sealing plug and anchor together with the suture slip-knot.

One skilled in the art would understand that the various aspects of the present invention described above can be combined and intermixed into various other arrangements and combinations, to achieve the desired sealing plug ease of ejection and ejection rate, and the desired loading of the sealing plug and knot into the carrier tube.

The above summary of the various representative embodiments of the invention is not intended to describe each illustrated embodiment or every implementation of the invention. Rather, the embodiments are chosen and described to that others skilled in the art may appreciate and understand the principles and practices of the invention. The figures in the detailed description that follows more particularly exemplify these embodiments.

BRIEF DESCRIPTION OF THE DRAWINGS

These as well as other objects and advantages of this invention will be more completely understood and appreciated by referring to the following more detailed description of the exemplary embodiments of the invention in conjunction with the accompanying drawings of which:

FIG. 11 is a perspective side view of a carrier tube according to one embodiment of the present invention;

FIG. 12 is a perspective side view of a carrier tube according to one embodiment of the present invention;

FIG. 13 is a perspective side view of a carrier tube according to one embodiment of the present invention;

FIG. 14 is a perspective side view of a carrier tube according to one embodiment of the present invention;

FIG. 19 is a perspective side view of a carrier tube according to one embodiment of the present invention;

FIG. 20 is a perspective side view of a carrier tube according to one embodiment of the present invention;

FIG. 21 is a perspective side view of a carrier tube according to one embodiment of the present invention;

FIG. 22 is a perspective side view of a carrier tube according to one embodiment of the present invention;

FIG. 24 is perspective side view of a carrier tube according to one embodiment of the present invention, the carrier tube produced by the heating element shown in FIG. 23 or the like;

FIG. 25 is a perspective side view of a carrier tube according to one embodiment of the present invention, wherein the carrier tube comprises two tubular members; and FIG. 26 is a perspective side view of a carrier tube according to one embodiment of the present invention, wherein the carrier tube comprises two tubular members.

Figure 1:
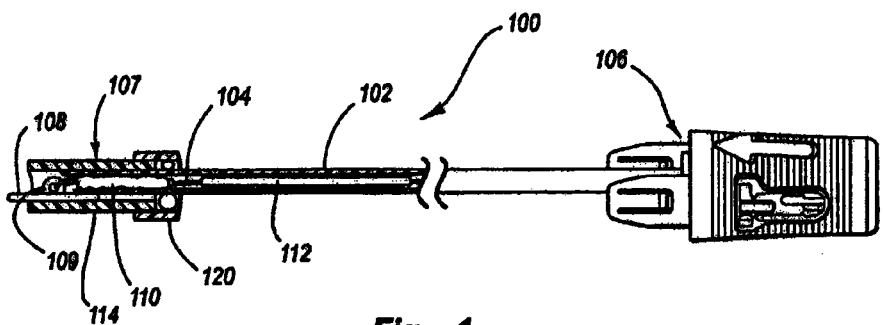
FIG. 1 is a side view, partly in section, of an internal tissue puncture closure tool.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives.

DETAILED DESCRIPTION

As mentioned above, vascular procedures generally require access to an artery through a puncture and puncture tract. Most often, the artery is a femoral artery. To close the puncture following completion of the vascular procedure, often a closure tool is used to sandwich the puncture or arteriotomy between an anchor positioned in the artery lumen and a sealing plug positioned in the puncture tract. However, sometimes the sealing plug may not seat properly against an exterior situs of the arteriotomy, for example, the sealing plug may not eject from a carrier tube properly. If the sealing plug does not seat against the arteriotomy, there is a potential for prolonged bleeding. Further, the sealing plug, along with the knot that is used to cinch together the sealing plug, can be difficult to load into the distal end of a carrier tube.

The present invention describes devices and methods to facilitate the proper ejection of the sealing plug, under varying conditions, and to thus reduce or eliminate misplacement of the sealing plug. Further, embodiments of the present invention facilitate loading of the sealing plug material and the accompanying cinching knot, or other retaining device, into the carrier tube, potentially decreasing manufacturing time. The sealing plug is made of a biocompatible resorbable material, for example, collagen. While the vascular instruments shown and described below include insertion sheaths and puncture sealing devices, the application of principles described herein are not limited to the specific devices shown. The principles described herein may be used with any vascular closure or similar device. For example, the device can be used to seal tissue punctures as well as arteriotomies.

As used in this specification and the appended claims, the term "tamp" or "tamping" is used broadly to mean packing down by one or a succession of blows or taps or smooth, steady pressure. A "tamping tube" is used broadly to mean any elongated device or series of devices, including any intermediate components, used alone or in combination to tamp something else directly or indirectly. The term "compaction tube" is used interchangeably with the term "tamping tube". The term "carrier tube" is used broadly to mean any elongated device or series of devices, including any intermediate components, used alone or in combination to carry or transport at least a sealing plug, directly or indirectly. "Engage" and "engageable" are also used broadly to mean interlock, mesh, or contact between two devices. A "spool" is a cylinder or other device on which something else is at least partially wound. A "lumen" refers to any open space or cavity in a bodily organ or device, especially in a blood vessel. "Automatic" means no action or intervention is required by a human operator. "Transduce" means to convert a force or other input energy in one form into output energy or forces of another form or direction. "Gradually" means advancing or progressing by regular or continuous degrees, or absent any abrupt changes. "Sudden" refers to a rapid, abrupt, or quick change. The words "including" and "having," as used in the specification, including the claims, have the same meaning as the word "comprising."

Referring now to the drawings, and in particular to FIGS. 1-4, a vascular puncture closure tool 100 is shown according to the prior art. The vascular puncture closure tool 100 includes a carrier tube 102 with a filament or suture 104 extending at least partially therethrough. The closure tool 100 also includes a first or proximal end 106 portion and a second or distal end portion 107. External to a distal end of the carrier tube 102 is an anchor 108. The anchor 108 is an elongated, stiff, low profile member including an eye 109 formed on the top surface, at approximately the middle, of the anchor 108. However, other shapes for the anchor 108 are possible. The anchor 108 is typically made of a biologically resorbable polymer.

The suture 104 is threaded through the anchor 108 and back to a bioresorbable sealing pad or plug; for example, a collagen plug 110. The collagen plug 110 may be comprised of randomly oriented fibrous material bound together by chemical means. The collagen plug 110 is slidingly attached to the suture 104 as the suture passes distally through the carrier tube 102, and as the suture traverses the anchor 108 through the eye 109 and reenters the carrier tube 102, it is securely slip knotted proximal to the collagen plug 110 to facilitate cinching of the collagen plug 110 when the closure tool 100 is properly placed and the anchor 108 has been deployed (see FIG. 4). The suture 104 may thus connect the anchor 108 and the sealing plug 110 in a pulley-like arrangement to cinch the anchor 108 and the sealing plug 110 together when the carrier tube 102 is pulled away from the anchor 108 and the sealing plug 110. The anchor 108 and the sealing plug 110 sandwich and lock together to seal the tissue puncture 118.

The carrier tube 102 typically includes a compaction device, tamping tube or compaction tube 112, disposed therein. The compaction tube 112 is slidingly mounted on the suture 104 and may be used by an operator to tamp the collagen plug 110 toward the anchor 108 at an appropriate time to seal a percutaneous tissue puncture.

Prior to deployment of the anchor 108 within an artery, the eye 109 of the anchor 108 rests outside the distal end portion 107 of the carrier tube 102. The anchor 108 may be temporarily held in place flush with the carrier tube 102 by a bypass tube 114 disposed over the distal end of the carrier tube 102.

Figure 2:
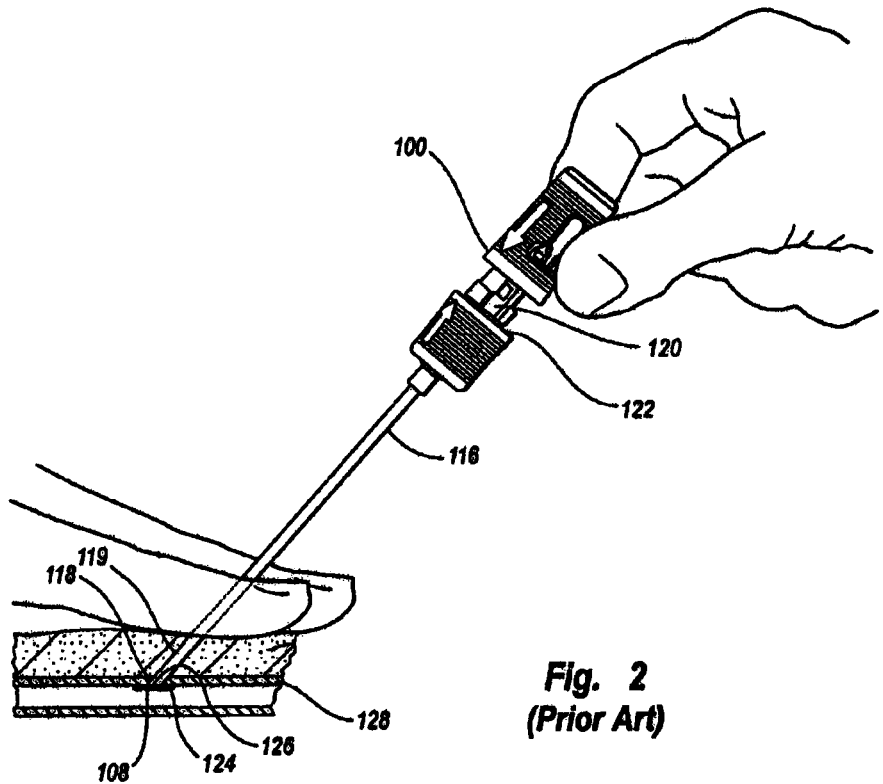
FIG. 2 is a side view of the tissue puncture closure tool of FIG. 1 inserted through an insertion sheath and engaged with an artery, the artery shown in section.
Figure 3:
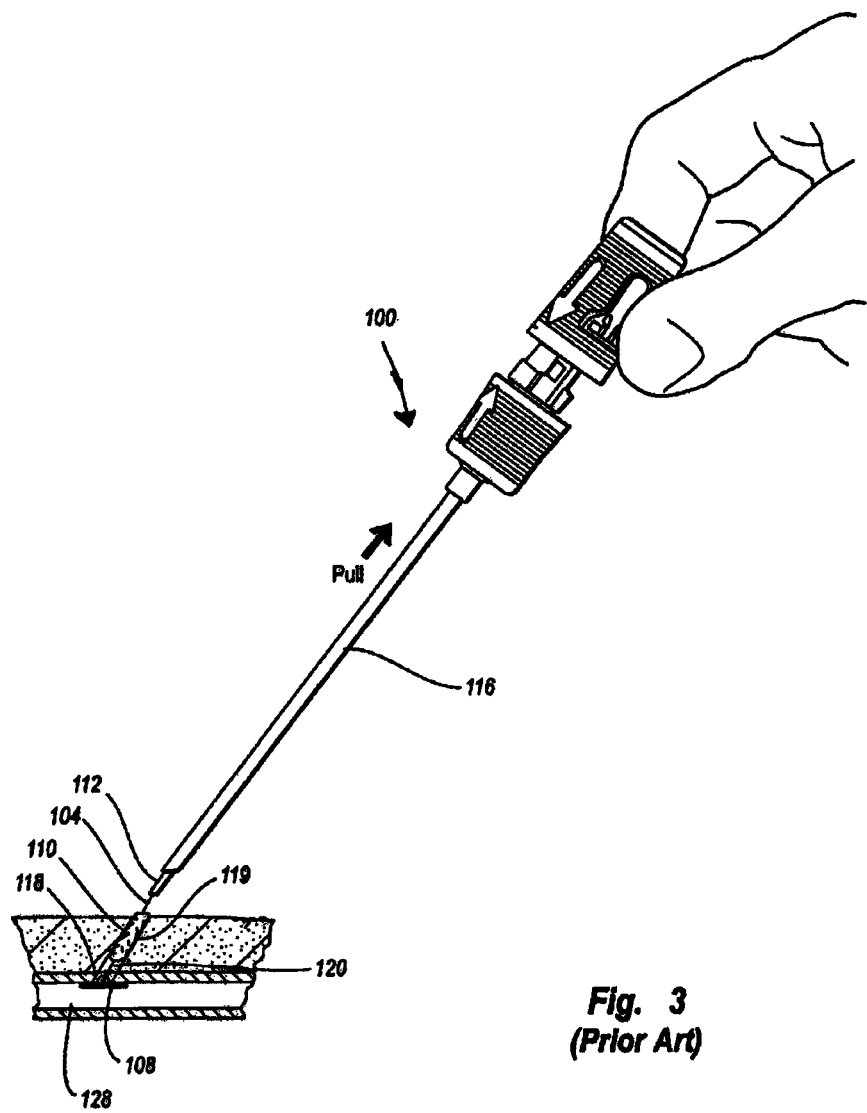
FIG. 3 is a side view of the tissue puncture closure tool, insertion sheath, and artery of FIG. 2, wherein the tissue closure tool and insertion sheath are being withdrawn from the artery to deploy a sealing plug, a collagen pad.
Figure 4:
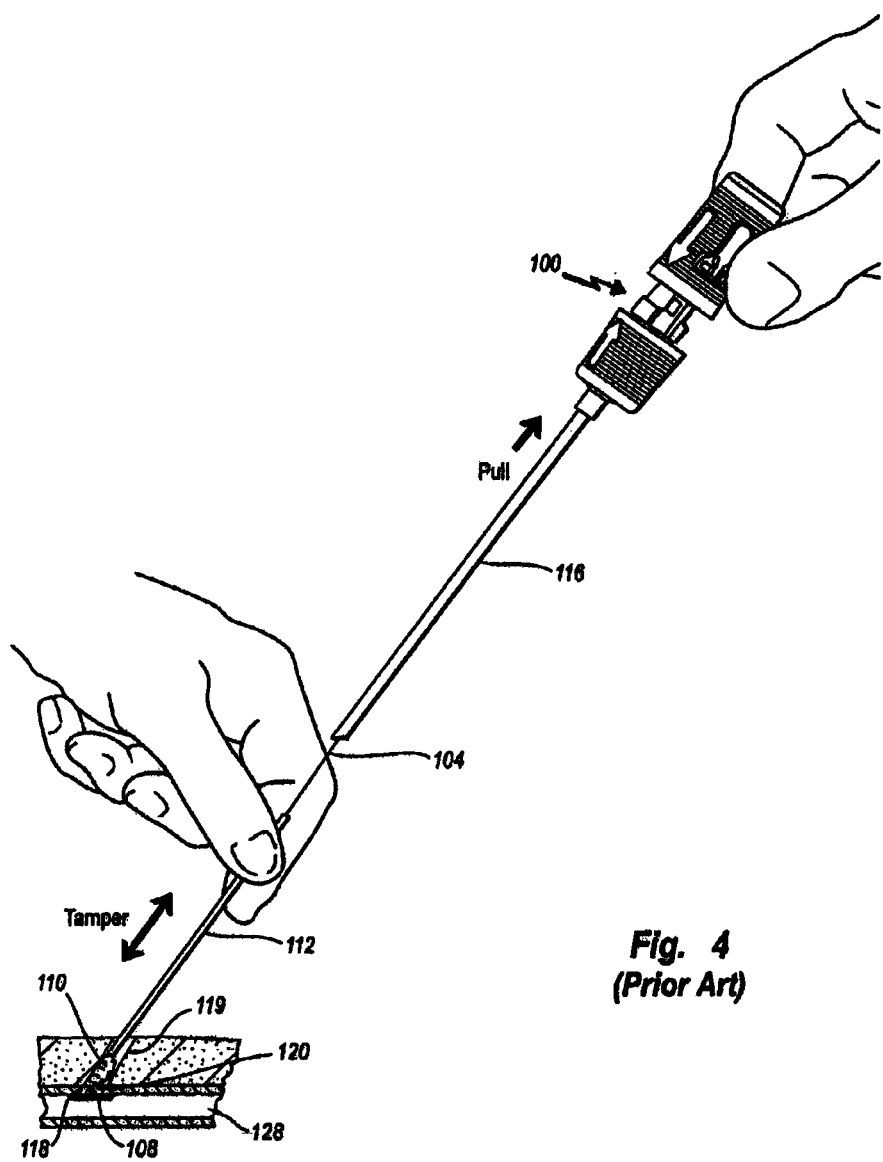
FIG. 4 is a side view of the tissue puncture closure tool, insertion sheath, and artery shown in FIG. 3 with a compaction device fully exposed and being used to tamp the collagen pad.

The flush arrangement of the anchor 108 and carrier tube 102 allows the anchor 108 to be inserted into an insertion sheath 116 as shown in FIGS. 2-4, and eventually through an tissue puncture 118. The insertion sheath 116 is shown in FIGS. 2-4 inserted through a percutaneous incision 119 and into an artery 128. The bypass tube 114 (FIG. 1) includes an oversized head 120 that prevents the bypass tube 114 from passing through an internal passage of the insertion sheath 116. Therefore, as the puncture closure tool 100 is inserted into the insertion sheath 116, the oversized head 120 bears against a surface 122 of the insertion sheath 116. Further insertion of the puncture closure tool 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114 as the insertion sheath 116 continues to limit anchor 108 movement.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 thereof. Typically, after the anchor 108 passes through the distal end 126 of the insertion sheath 116 and enters the artery 128, the anchor 108 is no longer constrained to the flush arrangement with respect to the carrier tube 102 and the anchor 108 deploys and rotates to the position shown in FIG. 2.

Referring next to FIGS. 3-4, with the anchor 108 deployed, the puncture closure tool 100 and the insertion sheath 116 are withdrawn together, forcing the collagen plug 110 through the tip of the carrier tube 102 and depositing it in the incision tract 119. The compaction tube 112 is also exposed. With the compaction tube 112 fully exposed as shown in FIG. 4, the compaction tube 112 is manually grasped, the collagen plug 110 is manually tamped, and the anchor 108 and collagen plug 110 are cinched together and held in place with the self-tightening slip-knot on the suture 104. Thus, the tissue puncture is sandwiched between the anchor 108 and the collagen plug 110, thereby sealing the puncture 118. The suture 104 is then cut and the incision tract 119 may be closed. The suture 104, anchor 108, and collagen plug 110 are generally made of resorbable materials, and remain in place while the puncture 118 heals, until the resorbable materials eventually resorb into the body.

Figure 5:
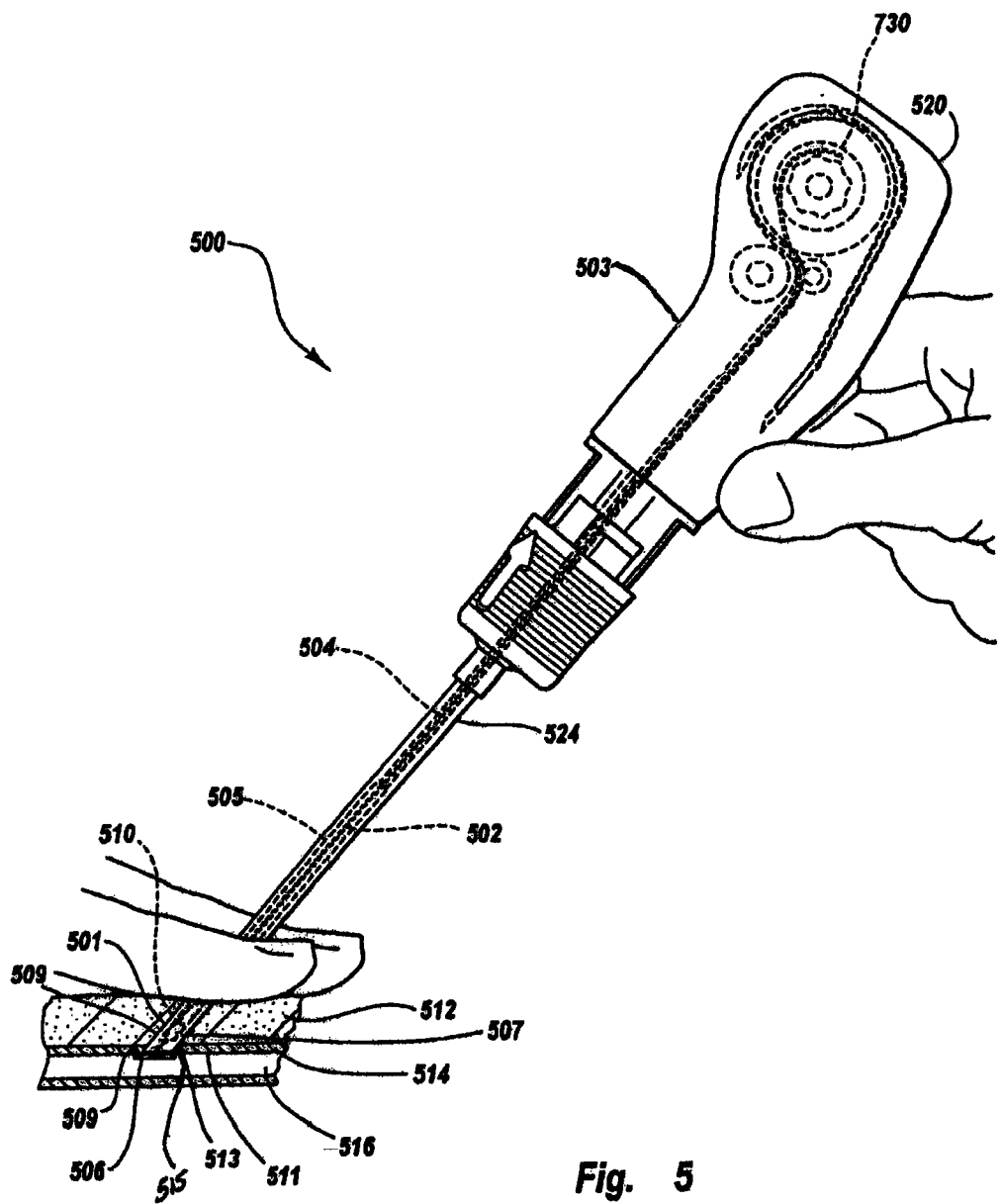
FIG. 5 is a side view of a tissue puncture closure tool with an automatic compaction mechanism shown engaged with an artery.
Figure 6:
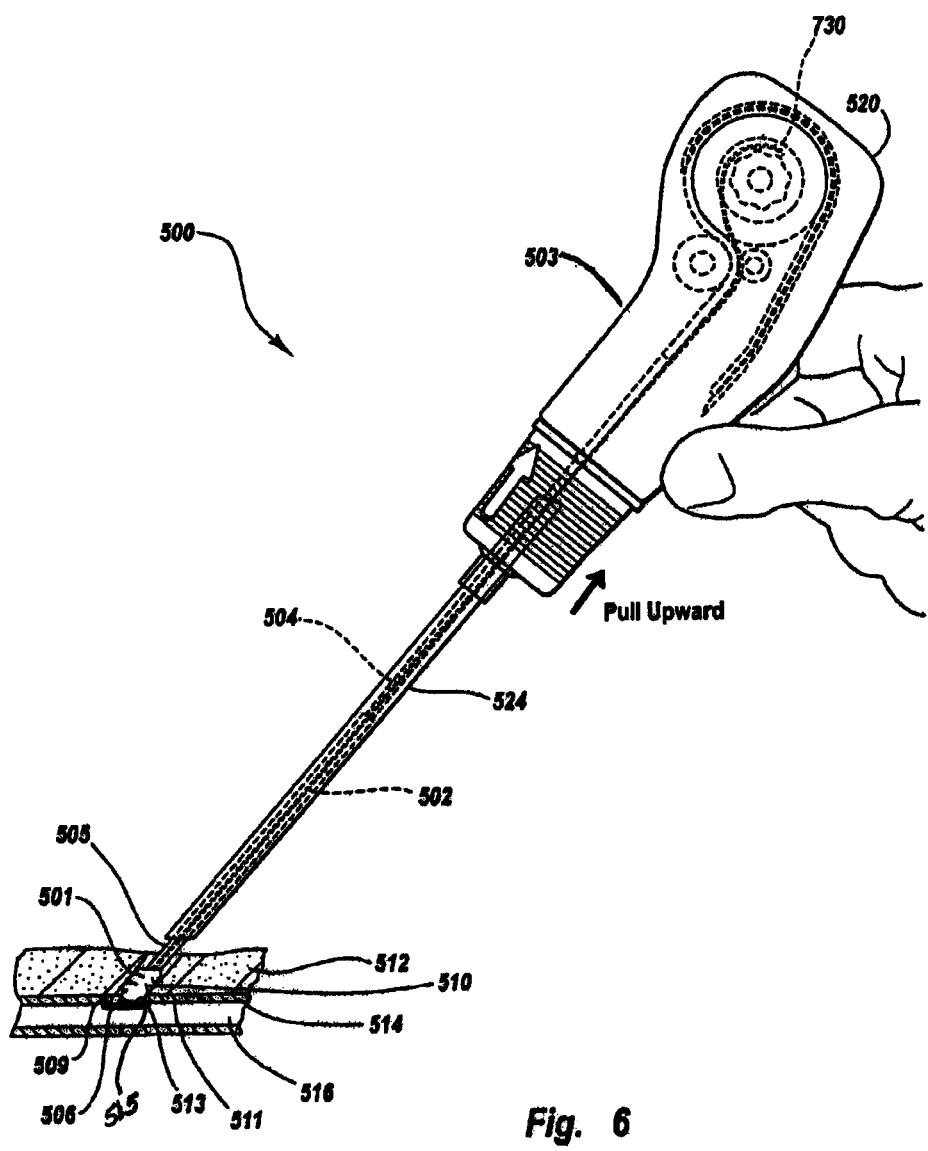
FIG. 6 is a side view of the tissue puncture closure tool of FIG. 5 being withdrawn from an artery

Referring to FIGS. 5 and 6, there is shown another vascular puncture closure tool. The tissue closure tool 500 includes a first or proximal end portion 503 and a second or distal end portion 507. A carrier tube 504 extends from the proximal end portion 503 to the distal end portion 507 and includes an outlet 515. The carrier tube 504 may be made of plastic or other material and is designed for insertion through a sheath 524 which is designed for insertion through a percutaneous incision 501 in a tissue layer 512 and into a lumen 516. According to FIG. 5, the lumen 516 defines an interior surface of a femoral artery 514.

The distal end portion 507 of the carrier tube 504 also includes an anchor 506 and a sealing plug 510. The anchor 506, in this instance, is an elongated, stiff, low-profile member preferably made of a biologically resorbable polymer. The sealing plug 510 is formed of a compressible sponge or foam, made of a hemostatic biologically resorbable material such as collagen, and may be configured in any shape so as to seal the tissue puncture 513. The sealing plug 510 and anchor 506 are connected to one another by a suture or filament 502 that is also biologically resorbable. The suture 502 extends distally from the first end 503 of the closure tool 500 through the carrier tube 504. The suture 502 is threaded through the sealing plug 510, then through an orifice (or orifices) in the anchor 506 and proximally back through the carrier tube 504 to the sealing plug 510. The suture 502 is preferably threaded through a perforation or series of perforations in the sealing plug 510. The suture 502 may also be threaded around itself to form a self-tightening slip-knot. The suture 502 thus connects the anchor 506 and the sealing plug 510 in a pulley-like arrangement that serves to cinch the anchor 506 and the sealing plug 510 together when the carrier tube 504 is pulled away from the anchor 506 and the sealing plug 510, sandwiching and locking the anchor 506 and plug 510 together and thereby sealing the tissue puncture 513.

The carrier tube 504 also includes a compaction device, such as a tamping tube or compaction tube 505, for tamping the sealing plug 510 along the suture 502 and against the anchor 506. The compaction tube 505 is shown located within the carrier tube 504 and proximal of the sealing plug 510. The compaction tube 505 is an elongated tubular member that may be rigid or flexible and formed of any suitable material. The suture 502 extends through the compaction tube 505 but is not directly connected thereto. Accordingly, the suture 502 and compaction tube 505 are free to slide past one another. According to the embodiment of FIG. 5, as the suture 502 extends beyond a proximal end of the compaction tube 505 and attaches to an automatic driving mechanism 730 located within a housing 520 at the first end portion 503 of the closure tool 500.

In practice, the carrier tube 504 of the closure tool 500 (containing the closure elements described above; the knot, suture, and the sealing plug; with the anchor positioned flush against the exterior of the carrier tube, held in position by a bypass tube) is inserted into an insertion sheath 524, which is already inserted within the artery 514. As the closure tool 500 and the associated closure elements are inserted into the insertion sheath 524, the anchor 506 passes through and out of a distal end 509 of the insertion sheath 524 and is inserted into the artery lumen 516. The closure tool 500 is then withdrawn from the insertion sheath 524 until the anchor 506 catches on the distal end 509 of the insertion sheath 524 and rotates to the position shown in FIG. 5. When resistance to further retraction of the closure tool 500 is felt by an operator, the closure tool 500 and the insertion sheath 524 are withdrawn together, causing the anchor 506 to anchor itself within the artery 514 against the artery wall 511. With the anchor 506 anchored within the artery 514 at the puncture site 513, further retraction of the closure tool 500 and insertion sheath 524 causes the sealing plug 510 to deploy from the distal end 507 of the carrier tube 504, thereby depositing the plug within the incision or puncture tract 501.

However, unlike the initial closure tool described above, and similar such closure tools that require a separate, manual tamping procedure following the deposition of the sealing plug 510, closure tool 500 automatically tamps the sealing plug 510. The automatic driving mechanism 730 drives, via a rack or compaction tube driver 744, the compaction tube 505 toward the sealing plug 510 automatically upon withdrawal of the closure tool 500 from the puncture tract 501, tamping the plug 510 toward the anchor 506 as shown in FIG. 6. The rack or compaction tube driver 744 can be coilable or can be a linear rack. The sealing plug 510 is tamped while the carrier tube 504 is still arranged adjacent to the puncture 513 in the femoral artery 514, reducing or eliminating any gaps that may otherwise occur between the sealing plug 510 and the puncture 513 in the femoral artery 514.

In addition, by placing tension on or pulling the suture 502 away from the puncture tract, the suture 502 cinches and locks (with a slip knot or the like) together the anchor 506 and the sealing plug 510, sandwiching the artery wall 511 between the anchor 506 and sealing plug 510. The force exerted by the compaction tube 505 and the cinching together of the anchor 506 and sealing plug 510 by the filament 502 also causes the sealing plug 510 to deform radially outward within the puncture tract and function as an anchor on the proximal side of the tissue puncture site 513.

The function of closure tools including the implementing principles described herein include closure of a percutaneous puncture or incision in tissue separating two internal portions of a living body, such as punctures or incisions in blood vessels, ducts or lumens, gall bladders, livers, hearts, etc.

As noted above, once the anchor 108/506 is anchored within the artery at the puncture site, further retraction of the closure tool 100/500 and insertion sheath 116/524 causes the sealing plug 110/510 to withdraw from the distal end of the carrier tube 102/504, thereby depositing the plug within the incision or puncture tract 118/501. For proper placement of the sealing plug 110/510, it is important for the sealing plug 110/510 to eject at the appropriate time from the distal end of the carrier tube 102/504. The ejection of the sealing plug 110/510 from the distal end of the carrier tube 102/504 can be affected by a number of variables, for example, the material composing the sealing plug 110/510, the amount of hydration of the sealing plug 110/510 prior to ejection, the configuration of the distal end of the carrier tube 102/504, the speed of pull-back of the closure device 100/500, to name a few. More control over sealing plug 110/510 deployment may be desired, to ensure successful ejection of the sealing plug 110/510, proper placement of the sealing plug 110/510 to prevent leakage, and proper expansion and compaction of the sealing plug 110/510. Improper deployment and positioning of the sealing plug 110/510 could result in poor sealing of the tissue puncture or incision, leading to body fluid leakage. Therefore, there is a need for a carrier tube 102/504 in a closure tool 100/500 that provides for improved control of the ejection and placement of the sealing plug 110/510 and, additionally, may reduce the manufacturing time required for the carrier tube assembly.

Figure 7:
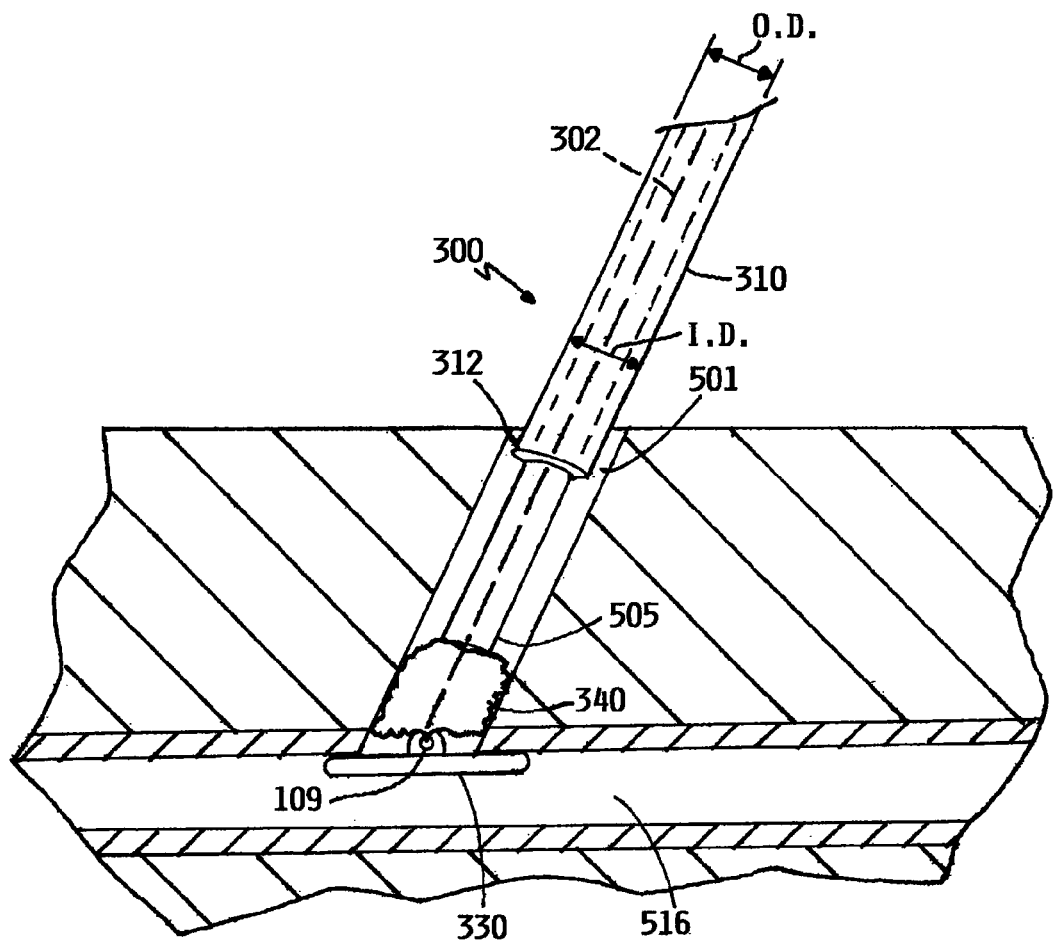
FIG. 7 is a perspective side view of a carrier tube showing placement of the anchor and sealing plug in a puncture tract.

Referring to FIG. 7, a carrier tube assembly 300 is shown, after the anchor 330 has been deployed into a lumen 516, in this case, an artery. The sealing plug 340 has already been deployed from the distal end 312 of the carrier tube 310. The carrier tube 310 generally has an outer diameter (O.D.) that is consistent throughout the length of the carrier tube 310, and an inner diameter (I.D.) that is consistent throughout the length of the carrier tube 310. The suture or filament 302 has already been tightened, to cinch the anchor 330 and the sealing plug 340 towards each other. A variety or biologically resorbable materials can be used for the sealing plug 340, however, in the examples provided herein, the sealing plug is made of collagen. As noted in FIG. 7, the sealing plug 340 is positioned adjacent to the exterior surface of the arteriotomy, opposite the lumen 516 or interior surface of the arteriotomy. The deployed anchor 330 is positioned on the lumen interior surface; the interior surface of the arteriotomy. The relative positioning of the sealing plug 340 and anchor 330 provides for a seal of the arteriotomy that is not prone to leak. Over time, the anchor 330 will resorb into the body, as will the sealing plug 340 and the suture 302.

Figure 8:
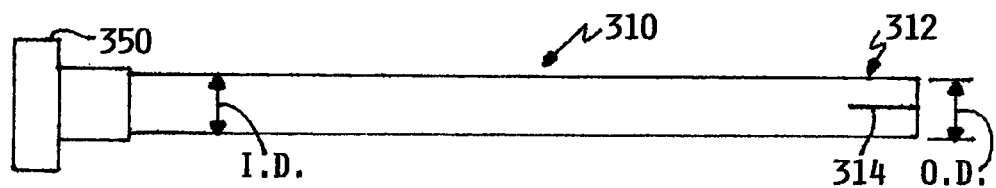
FIG. 8 is a perspective side view of a carrier tube according to one embodiment of the present invention.

Referring now to FIG. 8, a carrier tube 310 according to one embodiment of the invention is shown. The carrier tube refers to the tube utilized to carry at least the sealing plug and suture, and knot through a sheath and into a puncture tract or incision for deployment of the anchor, sealing plug, and knot. The proximal end of the carrier tube 310 is affixed to a hub 350. The hub 350 engages with the sheath structure of the closure device 100/500. The hub 350 can take on various shapes, to fit with the shape of the particular sheath structure of the closing device 100/500, and various shapes are contemplated. The carrier tube can have a "nest" formed into its outer surface (not shown) that conforms to the shape of the anchor to ensure a low profile (a bypass tube is slid over the anchor and carrier tube at the carrier tube's most distal end). The nest formed in the exterior of the carrier tube 310, along the distal end 312 of the carrier tube 310, can create some external force on the sealing plug 340 housed inside the carrier tube 340. The nest structure changes the carrier tube 310 profile at the distal end 312, by creating an indentation (nest) in the exterior of the carrier tube 310. Understandably, narrowing of the carrier tube 310 at the distal end 312 exerts some pressure on the sealing plug 340 that resides inside the carrier tube 310. The carrier tube 310 can include at least one slit 314 in the distal end 312 of the carrier tube 310, to assist in more easily loading and deploying the sealing plug 340 that is housed in the distal end 312 of the carrier tube 310. The at least one slit 314 ranges in length from about 0.04 inches. The at least one slit 314 ranges in length to about 1.8 inches, or even longer, dependent upon the length of the sealing plug 340. Thus, longer and shorter slits are contemplated. In one embodiment, the length of the at least one slit 314 ranges from about 0.6 to 0.8 inches. The shorter slit 314 length may be preferred if a faster hydrating material, for example, a faster hydrating collagen, is used as the sealing plug 340, or a shorter sealing plug 340 is used. The shorter slit 314 allows for less exposure of the collagen plug 340 to moisture, and thus the collagen plug 340 will not hydrate so much that ejection of the collagen sealing plug 340 becomes difficult. However, if a slower hydrating collagen and/or a longer sealing plug 340 is used, then the at least one slit 314 in the distal end 312 of the carrier tube 310 can be in the range of longer lengths. The slower hydrating collagen sealing plug 340 will not respond as quickly to the increased moisture that may be present due to the longer slit 314 lengths. A slightly hydrated sealing plug 340 is generally easier to deploy than a sealing plug 340 that is completely dry, and also tends to compact better within the puncture tract 501.

The at least one slit 314 also can ease loading of the collagen sealing plug 340, the suture 304, and the knot 305, into the distal end 312 of the carrier tube 310. The at least one slit 314 provides for some flexibility and expansion in the distal end 312 of the carrier tube 310, as the puncture tract closure elements (collagen sealing plug 340, suture 304, and knot 305) are loaded into the carrier tube 310. However, the at least one slit 314 has enough memory to securely hold the puncture tract closure elements within the distal end 312 of the carrier tube 310.

Figure 9:
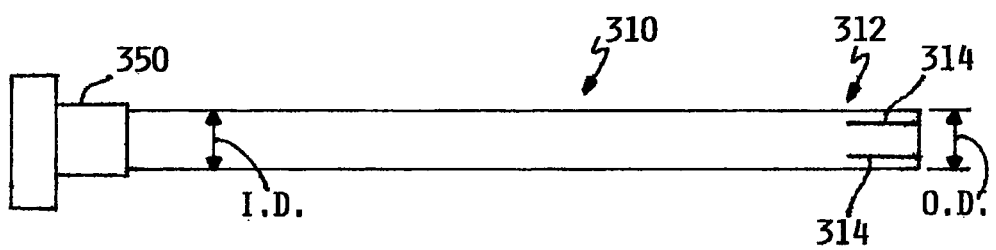
FIG. 9 is a perspective side view of a carrier tube according to one embodiment of the present invention.

FIG. 9 shows the carrier tube including a plurality of slits 314. The slits 314 can be positioned equally spaced around the circumference of the distal end 312 of the carrier tube 310, or in some other pattern. The number and position of the slits 314 can vary due to the nature of the sealing plug 340 being used; for example, the material of the plug 340, dependent upon its hydration rate, can require more or fewer slits 314, and the configuration of the plug 340 may require more distal end 312 flexibility. The length of the slits 314 can also vary, along with the number of slits and the nature of the sealing plug 340, such that loading of the closure elements in the distal end 312 of the carrier tube 310, retention of the closure elements in the carrier tube 310 prior to ejection, and the proper deployment of the sealing plug 340 are all facilitated.

Figure 10:
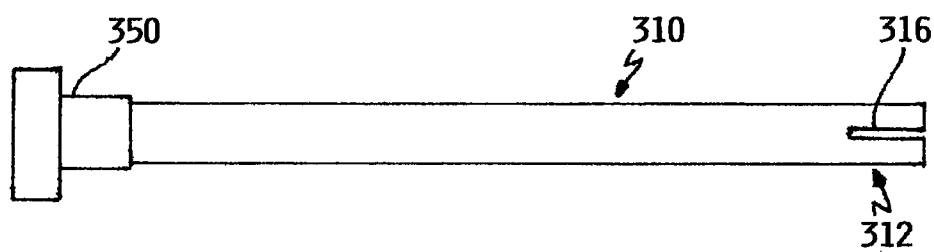
FIG. 10 is a perspective side view of a carrier tube according to one embodiment of the present invention.
Figure 15:
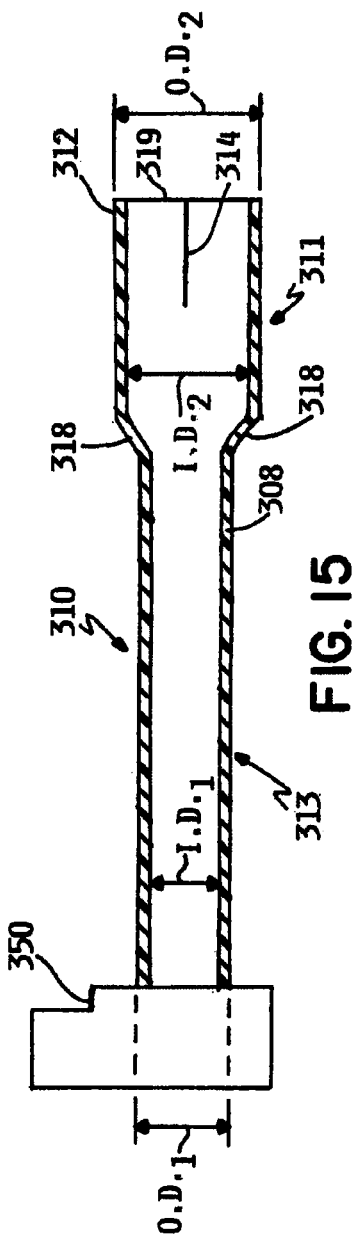
FIG. 15 is a perspective side view of a carrier tube according to one embodiment of the invention.
Figure 16:
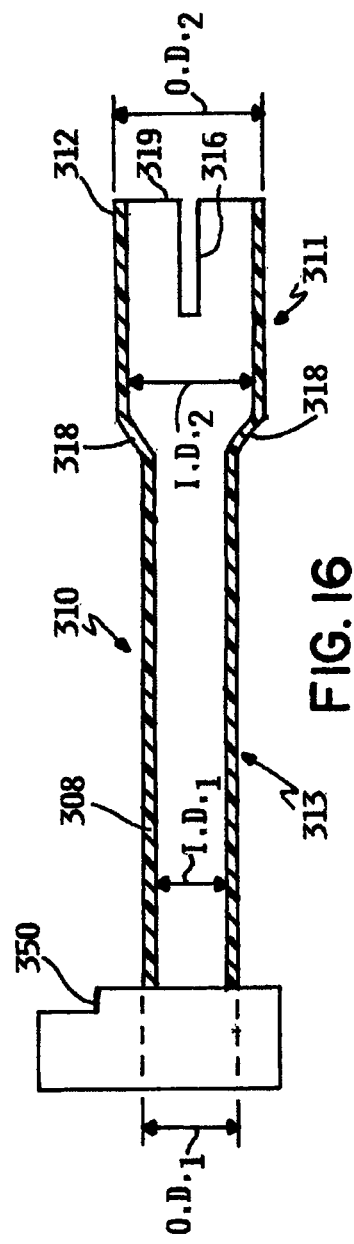
FIG. 16 is a perspective side view of a carrier tube according to one embodiment of the present invention.
Figure 17:
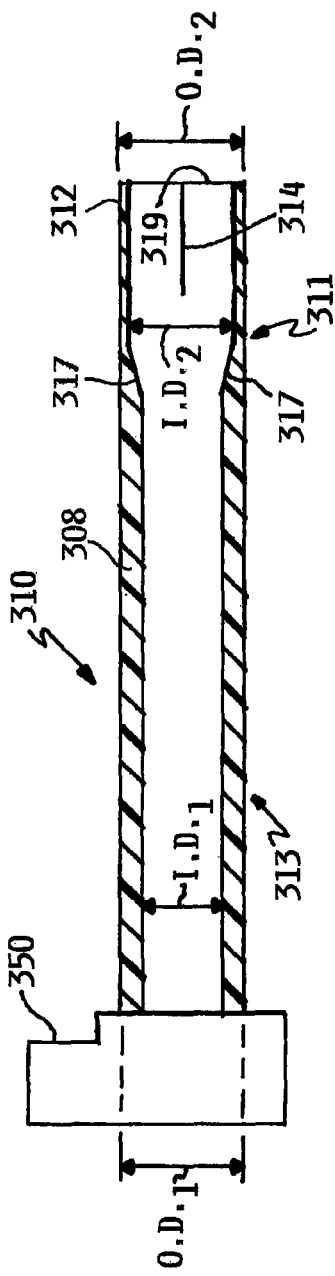
FIG. 17 is a perspective side view of a carrier tube according to one embodiment of the present invention.
Figure 18:
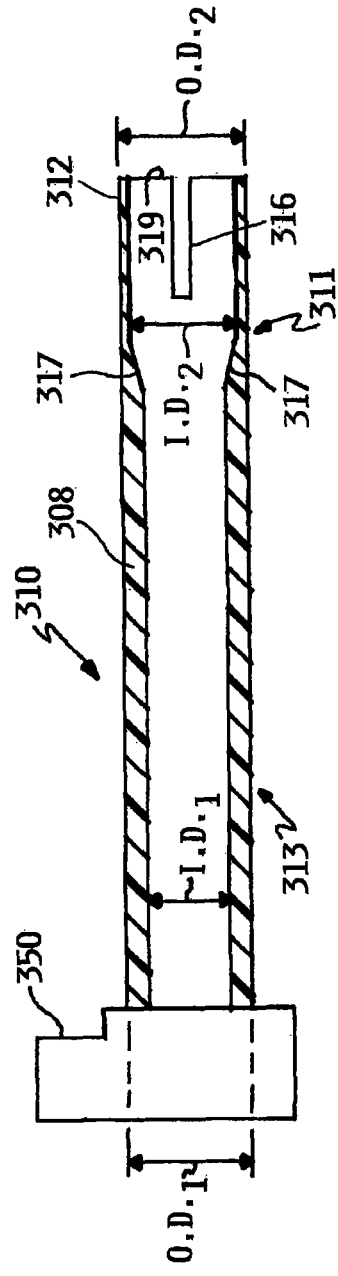
FIG. 18 is a perspective side view of a carrier tube according to one embodiment of the present invention.

Referring now to FIG. 10, another embodiment of the invention is shown. FIG. 10 shows a carrier tube 310, including a hub 350, where the distal end 312 of the carrier tube 310 can include at least one slot 316. The slot 316 can be formed by actual removal of a section of the carrier tube 310, with width. Cuts can be made along the longitudinal axis of the carrier tube 310, connected by, for example, cutting laterally, and a section of the material of the carrier tube 310 can be removed to form the slot 316. The slot 316 can also be formed, for example, by the two cuts meeting at a point, and the section of material of the carrier tube 310 being removed. The slot 316 can extend generally from about 0.50 to about 1.0 inches or more into the distal end 312 of the carrier tube 310. In one embodiment, the length of the at least one slot 316 ranges from about 0.75 inches to about 0.85 inches. However, shorter and longer slot 316 lengths are contemplated, to suit the needs of the sealing plug 340 and other closure elements. The shorter slot 316 length may be preferred when a faster hydrating bioresorbable material is used as the sealing plug 340. For example, a faster hydrating collagen material may require a shorter slot 316 so that the collagen sealing plug 340 did not hydrate to the extent that deployment of the sealing plug 340 would be hindered and/or placement of the sealing plug in the puncture tract or incision would not be as desired. The shorter slot 316 allows for less exposure of the sealing plug 340, and thus limiting the exposure of the collagen sealing plug 340, for example, to moisture. However, if a slower hydrating material is used for the sealing plug 340, e.g. a slower hydrating collagen, then the at least one slot 316 in the distal end 312 of the carrier tube 310 can be in the range of the longer lengths. The slower hydrating collagen sealing plug 340 will not respond as quickly to the increased moisture that may be present due to the longer slot 314 lengths. Further, the width of the slot 316 must be taken into consideration as well, with respect to exposing the sealing plug 340 to moisture. As noted with the slits 314 above, the carrier tube 310 can include a plurality of slots 316, of similar length or of various lengths. The slots 316 can be positioned about the circumference of the distal end 312 of the carrier tube 310 to achieve the desired rate of hydration.

The length, width, number and positioning of the slots 316 about the circumference of the distal end 312 of the carrier tube 310 can also facilitate loading the closure elements into the distal end 312 of the carrier tube 310. However, the number, placement, and characteristics of the slots 316 are selected to maintain the closure elements within the distal end 312 of the carrier tube 310 until the anchor 330 and sealing plug 340 are ready to be deployed. In another embodiment of the invention, the distal end 312 of the carrier tube 310 can include at least one slit 314 and at least one slot 316.

In another embodiment of the invention, the inner diameter I.D.1 of the proximal portion 313 of the carrier tube 310 is smaller than the inner diameter I.D.2 of the distal portion 311 of the carrier tube 310. As a result of a wider inner diameter I.D.2 in the distal portion 311 of the carrier tube 310, the aperture 319 at the distal end 312 of the carrier tube 310, through which the puncture tract closure elements are loaded, is wider than the aperture 319 in the carrier tube 310 shown in FIGS. 8-10, where the inner diameter is generally consistent throughout the length of the carrier tube 310 and the outer diameter is generally consistent throughout the length of the carrier tube 310. Generally, the inner diameter I.D.2 of the distal portion 311 of the carrier tube is about 0.002-about 0.01 inches larger than the inner diameter I.D.1 of the proximal portion 313 of the carrier tube 310. The larger inner diameter I.D.2 distal portion 311 provides for a larger space in which to load the puncture tract closure elements, thus potentially decreasing the production time required to produce the carrier tube assembly. Further, the larger aperture 319 allows for less friction between the carrier tube 310 and the collagen sealing plug 340 during device deployment, thus facilitating the ejection of the sealing plug 340 at the appropriate time and in the appropriate position. The above described configuration can be used with a material having either a slower rate of hydration or a faster rate of hydration, dependent upon the other structures such as slits and/or slots in the distal end 312 of the carrier tube 310. Generally, however, a shorter slit or slot will be paired with the larger aperture 319 if a faster hydrating material is used for the sealing plug 340, and a longer slit or slot will be paired with a larger aperture 319 if a slower hydrating material is used for the sealing plug 340. Without being bound to a particular theory, generally, the collagen sealing plug material, after being loaded into the distal end 312 of the carrier tube 310, may relax and rebound or expand slightly which may cause pores in the distal end of the collagen sealing plug 340 to become more open. Generally, the very distal end of the collagen sealing plug 340 may slightly hydrate before ejection, facilitating easier and proper deployment, positioning, and compaction of the sealing plug 340 in the puncture tract. The rate of hydration of the collagen of the sealing plug 340 may limit which collagen, or other material, is preferred to be used with the above described carrier tube 310 structure.

Referring to FIG. 11, there is shown one embodiment of the invention, wherein the proximal portion 313 of the carrier tube 310, as it approaches the distal portion 311 of the carrier tube 310, forms a shoulder 318, the shoulder 318 leading to the distal portion 311 of the carrier tube 310. The shoulder 318 forms a transition from the proximal portion 313 of the carrier tube 310 to the distal portion 311 of the carrier tube 310. The inner diameter and the outer diameter of the carrier tube 310 are consistent along the length of the carrier tube 310, except for the last about 1.5-0.25 inches, or longer, of the distal portion 311 of the carrier tube 310. The inner diameter I.D.1 of the proximal portion 313 of the carrier tube 310 is smaller than the inner diameter I.D.2 of the distal portion 311 of the carrier tube 310, and the outer diameter O.D.1 of the proximal portion 313 of the carrier tube 310 is smaller than the outer diameter O.D.2 of the distal portion 311 of the carrier tube 310. Generally, the inner diameter I.D.2 and outer diameter O.D.2 of the distal portion 311 of the carrier tube are 0.002-0.008 inches larger than the inner diameter I.D.1 and outer diameter O.D.1 of the proximal portion 313 of the carrier tube 310, respectively. As a result of a wider inner and outer diameter of the distal portion 311 of the carrier tube 310, the aperture 319 at the distal end 312 of the carrier tube 310 is wider than the aperture 319 in the carrier tube 310 where the inner diameter is generally consistent throughout the length of the carrier tube 310 and the outer diameter is generally consistent throughout the length of the carrier tube 310, as shown in FIGS. 8-10.

In another embodiment of the invention, as shown in FIG. 12, the proximal portion 313 of the carrier tube 310, as it approaches the distal portion 311 of the carrier tube 310, forms a shoulder 317 internal to the carrier tube 310, the shoulder 317 area leading to the distal portion 311 of the carrier tube 310. The shoulder 317 is formed as part of the internal wall surface 309 of the carrier tube 310, the internal wall surface 309 defining the lumen of the carrier tube 310. The shoulder 317 forms a transition from the proximal portion 313 of the carrier tube 310 to the distal portion 311 of the carrier tube 310. The inner diameter I.D.1 of the proximal portion 313 of the carrier tube 310 is smaller than the inner diameter I.D.2 of the distal portion 311 of the carrier tube 310. However, the outer diameter O.D.1 of the proximal portion 313 of the carrier tube 310 is substantially the same as the outer diameter O.D.2 of the distal portion 311 of the carrier tube 310. Thus, the outer diameter of the carrier tube 310 is consistent along the length of the carrier tube 310. Generally, the inner diameter I.D.2 of the distal portion 311 of the carrier tube 310 is about 0.002-0.01 inches larger than the inner diameter I.D.1 of the proximal portion 313 of the carrier tube 310. The inner diameter of the carrier tube 310 is consistent along the length of the carrier tube 310, except for the last about 1.5-0.25 inches of the distal portion 311 of the carrier tube 310. The wider inner diameter I.D.2 is accommodated by the walls 308 of the distal portion 311 of the carrier tube 310 being thinner than the walls 308 of the proximal portion 313 of the carrier tube 310. As a result of a wider inner diameter in the distal portion 311 of the carrier tube 310, the aperture 319 at the distal end 312 of the carrier tube 310 is wider than the aperture 319 in the carrier tube 310 where the inner diameter is generally consistent throughout the length of the carrier tube 310 as shown in FIGS. 8-10.

Referring now to FIG. 13, there is shown an embodiment of the invention, wherein the proximal portion 313 of the carrier tube 310, as it approaches the distal portion 311 of the carrier tube 310, begins to expand outwardly or flare, leading to a distal portion 311 of the carrier tube 310 with a wider inner diameter I.D.2 than the inner diameter I.D.1 of the proximal portion 313 of the carrier tube 310. The inner diameter and the outer diameter of the carrier tube 310 are consistent along the length of the carrier tube 310, except for the last about 1.5-0.25 inches of the distal portion 311 of the carrier tube 310. The gradual flaring forms a transition from the proximal portion 313 of the carrier tube 310 to the distal portion 311 of the carrier tube 310. The inner diameter I.D.1 of the proximal portion 313 of the carrier tube 310 is smaller than the inner diameter I.D.2 of the distal portion 311 of the carrier tube 310, and the outer diameter O.D.1 of the proximal portion 313 of the carrier tube 310 is smaller than the outer diameter O.D.2 of the distal portion 311 of the carrier tube 310. Generally, the inner diameter I.D.2 and outer diameter O.D.2 of the distal portion 311 of the carrier tube are about 0.002-0.01 inches larger than the inner diameter I.D.1 and outer diameter O.D.1 of the proximal portion 313 of the carrier tube 310, respectively. As a result of a wider inner and outer diameter in the distal portion 311 of the carrier tube 310, the aperture 319 at the distal end 312 of the carrier tube 310 is wider than the aperture 319 in the carrier tube 310 where the inner diameter is generally consistent throughout the length of the carrier tube 310 and the outer diameter is generally consistent throughout the length of the carrier tube 310, as shown in FIGS. 8-10. As compared to the carrier tube 310 of FIG. 11, the carrier tube 310 gradually flares to the final inner diameter I.D.2 and outer diameter O.D.2.

In yet another embodiment, as shown in FIG. 14, the proximal portion 313 of the carrier tube 310, as it approaches the distal portion 311 of the carrier tube 310, begins to expand outwardly or flare, leading to a distal portion 311 of the carrier tube 310 with a wider inner diameter I.D.2 than the inner diameter I.D.1 of the proximal portion 313 of the carrier tube 310, similar to FIG. 13. However, the gradual flaring of the distal portion 311 of the carrier tube 310 occurs at the expense of the thickness of the carrier tube 310 walls 308 in the distal portion 311 of the carrier tube 310. The outward flaring is formed as part of the carrier tube 310 wall is thinned, with the expanded lumen of the carrier tube 310 in the distal end 311 of the carrier tube 310 occupying the space once occupied by part of the internal wall 308 of the carrier tube 310. The inner diameter I.D.1 of the proximal portion 313 of the carrier tube 310 is smaller than the inner diameter I.D.2 of the distal portion 311 of the carrier tube 310. However, the outer diameter O.D.1 of the proximal portion 313 of the carrier tube 310 is substantially the same as the outer diameter O.D.2 of the distal portion 311 of the carrier tube 310. Thus, the outer diameter of the carrier tube 310 is consistent along the length of the carrier tube 310. Generally, the inner diameter I.D.2 of the distal portion 311 of the carrier tube is about 0.002-0.01 inches larger than the inner diameter I.D.1 of the proximal portion 313 of the carrier tube 310. The wider inner diameter I.D.2 is accommodated by the walls 308 of the distal portion 311 of the carrier tube 310 being thinner than the walls 308 of the proximal portion 313 of the carrier tube 310. The inner diameter of the carrier tube 310 is consistent along the length of the carrier tube 310, except for the last about 1.3-0.25 inches of the distal portion 311 of the carrier tube 310. As a result of a wider inner diameter in the distal portion 311 of the carrier tube 310, the aperture 319 at the distal end 312 of the carrier tube 310 is wider than the aperture 319 in the carrier tube 310 where the inner diameter is generally consistent throughout the length of the carrier tube 310 as shown in FIGS. 8-10.

The carrier tubes 310 described in FIGS. 11-14 each include a wider aperture 319 at the distal end 312 of the carrier tube 310 than in the carrier tubes 310 shown in FIGS. 8-10. As noted above, the wider inner diameter I.D.2 distal portion 311 provides for a larger space in which to load the puncture tract closure elements, thus potentially decreasing the production time required to produce the carrier tube assembly 300. Further, the larger aperture 319 allows for increased exposure of the very distal end of the sealing plug 340 to moisture, thus facilitating the ejection of the sealing plug 340 at the appropriate time and in the appropriate position. Further, generally the compaction of the collagen sealing plug 340 in the puncture tract is improved when the sealing plug 340 has already been somewhat hydrated, as described above. There is a balance to be achieved between the hydration rate of the material of the sealing plug 340 and the shape and structure of the carrier tube 340 that is to be used.

A rapidly hydrating material, including a rapidly hydrating collagen, can be used as a sealing plug 340 in such an expanded-end carrier tube. However, the slit 316 that would be part of the carrier tube 340 structure would likely be a shorter slit 316. The shorter slit 316 would still assist in easing the loading of the puncture tract closure elements into the carrier tube 340, but would not facilitate as much moisture entry as compared to a longer slit 314. Thus the sealing plug 340 would not hydrate too rapidly or too much and, therefore, undue force would not be used to deploy the sealing plug 340. The size of the aperture 319 at the distal end 312 of the carrier tube 310 can be varied to accommodate sealing plugs 340 of varying rates of hydration. For example, the above described configuration, with a larger aperture 319, can be used with a material having a slower rate of hydration, especially if a longer slit 314 or slot 316 is part of the distal end 312 structure. Further, the wider inner diameter I.D.2 facilitates earlier or proper ejection of the sealing plug 340 in the case of a slow pull back of the closure device. Generally, a larger aperture 319 facilitates easier loading of the puncture tract closure elements, easier and properly placed deployment of the sealing plug 340, and improved compaction of the sealing plug 340 in the puncture tract 118/501.

As noted above, the carrier tubes shown in FIGS. 11-14 can be further modified by the addition of at least one slit 314 and/or at least one slot 316, the slit 314 or slot 316 as described in the embodiments shown in FIGS. 8-10. FIGS. 15-22 show examples of additional embodiments of the invention, wherein the carrier tube 310 includes a wider inner diameter I.D.2 in the distal portion 311 of the carrier tube 310 than in the proximal portion 313 of the carrier tube, along with at least one slit 314 and/or at least one slot 316 in the distal end 312 of the carrier tube 310. However, the at least one slit 314 and/or the at least one slot 316 may be of a shorter length as compared to a slit 314 or a slot 316 included in a carrier tube 310 which does not include a wider inner diameter I.D.2. For example, the length of the slit 314 or slot 316 can range from 0.2-0.5 inches, and preferably 0.30-0.40 inches. The combination of a wider distal portion 311 inner diameter I.D.2, and its measurement, and at least one slit 314 or slot 316, and its length, can be varied to achieve the desired carrier tube 310 structure and function. It should be noted that there are practical limitations to the width of the distal end 312 of the carrier tube 310, as it relates to the size of the sheath and puncture/incision, as well as to the size of the bypass tube 114 and the oversized head 120 of the bypass tube 114, without altering either of the bypass tube 114 or the oversized head 120. However, the bypass tube 114 and oversized head 120 can be altered to accommodate a wider distal end 312 of the carrier tube 310.

Figure 23:
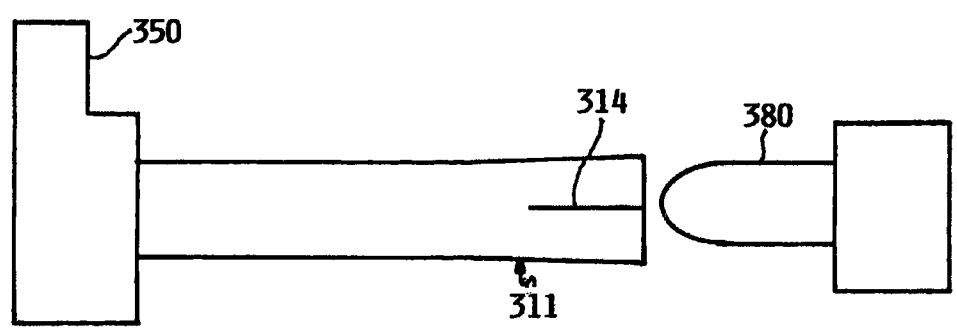
FIG. 23 is a perspective side view of a carrier tube according to one embodiment of the present invention, and a heating element.
Figure 24:
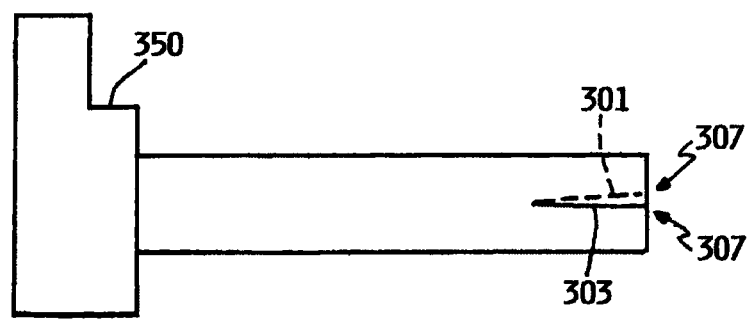

In another embodiment of the invention, a carrier tube 310 with a wider inner diameter I.D.2 than proximal inner diameter I.D.1 can also include an overlapping slit 307. The initial carrier tube 310 can be of the type as shown in FIG. 11, 12, 13, or 14. In this example, the carrier tube from FIG. 13 is used as the carrier tube 310 which will then have an overlapping slit 307 inserted into its structure, however other carrier tubes 310 having a wider distal portion 311 inner diameter I.D.2 than proximal portion 313 inner diameter I.D.1 can be used. Referring to FIG. 23, there is shown a carrier tube 310 with a gradually flaring distal portion 311 approaching a heated pin 380. A slit 314 is cut into the distal end 312 of the carrier tube 310. The distal end 312 of the carrier tube 310 is then pushed over the heated pin 380 where heat and radial force causes the slit edges 301, 303 to overlap. Circumferential force is applied to the outer diameter of the distal end 312 of the carrier tube, wherein the elements applying the force may also be heated. For example, the carrier tube distal end 312 can be heat shrunk with circumferential pressure being applied by a hot jaw near the polymer glass transition temperature. Alternatively, an annealing process can be used to cause the slit edges 301, 303 to overlap. The temperature used in the annealing process would be about one-fourth (¼) to one-half (½) of the polymer glass transition temperature. The overlapping slit edges 301, 303 prevent early hydration of the sealing plug 340. Due to the overlap of the slit edges 301, 303, the slit lengths can be longer to accommodate loading of the puncture tract closure elements in the distal end 312 of the carrier tube 310, yet the overlapping slit edges 310, 303 can prevent the early hydration and potential subsequent improper deployment of the sealing plug 340.

In yet another embodiment, as shown in FIG. 25, the carrier tube 310 comprises two tubular members 10, 20, which are fixed together, forming a continuous lumen therethrough. The inner diameter I.D.2 of the tubular member 20 forming the distal portion 311 of the carrier tube 310 transitions from a smaller inner diameter at the proximal portion of the tubular member 20 to a larger inner diameter at the distal portion of the tubular member 20, where the distal inner diameter I.D.2 is greater than the inner diameter I.D.1 of the tubular member 10 forming the proximal portion 313 of the carrier tube 310. The outer diameter O.D.2 of the tubular member 20 forming the distal portion 311 of the carrier tube is larger than the outer diameter O.D.1 of the tubular member 10 forming the proximal portion 313 of the carrier tube 310. Alternatively, although the inner diameter I.D.1 of tubular member 10, forming the proximal portion 313 of the carrier tube 310 is smaller than the inner diameter I.D.2 of tubular member 20, the two outer diameters, O.D.1 and O.D.2, can be substantially the same, as shown in FIG. 26. The thinner walls 308 of tubular member 20 can accommodate the larger inner diameter I.D.2, yet provide a fixing surface to be able to affix the distal end of tubular member 10 to the proximal end of tubular member 20. The distal end 312 of the carrier tube can, alternatively, include at least one slit 314 and/or slot 316.

The various characteristics of the carrier tube 310, for example, the size of the inner diameter I.D.2 of the distal portion 311 of the carrier tube, the size of the aperture 319 in the distal end 312 of the carrier tube 310, the presence and number of slits 314 and/or slots 316 in the distal end 312 of the carrier tube, the length of the slit(s) 314 and/or slot(s) 316, can be varied and combined in various combinations, to accommodate the hydration rate of the material of the sealing plug 340. Generally, at least some slight hydration of the sealing plug 340 can assist in easier and proper deployment of the sealing plug 340, and compaction of the sealing plug 340 in the puncture tract 118/501 is generally improved. Care must be taken that the sealing plug 340 is not hydrated too much, resulting in poor deployment and/or the use of excess force to deploy the sealing plug 340. Further, the use of a carrier tube 310 with a wider distal portion 311 inner diameter I.D.2 can assist in the loading of the puncture tract closure elements, as can the addition of slits or slots to the distal end 312 of the carrier tube 310. For example, a slower hydrating sealing plug 340 may perform well in a carrier tube 310 where the inner diameter I.D.2 is relatively larger and the distal end 312 of the carrier tube includes a slit 314 or slot 316, and perhaps a slightly longer slit 314 or slot 316, as compared to a faster hydrating sealing plug 340.

The carrier tubes 310 described herein can be formed by various techniques. For example, the carrier tubes 310 described above and shown in FIGS. 25 and 26 can be bonded together. Further, the carrier tubes 310 can be manufactured using techniques such as bump extrusion, forming, molding (for example, injection molding or blow molding), or other such similar processes known to one skilled in the art.

The preceding description has been presented only to illustrate and describe exemplary embodiments of invention. It is not intended to be exhaustive or to limit the invention to any precise form disclosed. Many modifications and variations are possible in light of the above teaching. Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents.

What is claimed is:

1. A carrier tube, comprising:
   a proximal portion having an inner diameter, an outer diameter, and a proximal portion wall thickness defined by the proximal portion inner diameter and outer diameter, the proximal portion being affixed to a hub;
   a distal portion having an inner diameter, an outer diameter, and a distal portion wall thickness defined by the distal portion inner diameter and outer diameter, wherein the distal portion inner diameter is larger than the proximal portion inner diameter;
   a shoulder positioned between a cylindrical portion of the carrier tube proximal portion and a cylindrical portion of the carrier tube distal portion;
   at least one slit or slot formed in a distal-most edge of the distal portion, the slot extending in a proximal direction from the distal-most edge of the distal portion; and
   wherein the distal portion wall thickness is thinner than the proximal portion wall thickness.

2. The carrier tube of claim 1, wherein the distal portion outer diameter is substantially equal to the proximal portion outer diameter.

3. The carrier tube of claim 1, wherein the shoulder provides a transition from the carrier tube proximal portion to the carrier tube distal portion.

4. The carrier tube of claim 1, wherein a transition from the carrier tube proximal portion to the carrier tube distal portion includes the carrier tube wall thickness gradually becoming thinner.

5. The carrier tube of claim 1, wherein the distal portion outer diameter is larger than the proximal portion outer diameter.

6. The carrier tube of claim 1, wherein a first edge of the at least one slit overlaps a second edge of the at least one slit.

7. A carrier tube, comprising:
   a proximal portion having an inner diameter, an outer diameter, and a proximal portion wall thickness defined by the proximal portion inner diameter and outer diameter, the proximal portion being affixed to a hub;
   a distal portion having an inner diameter, an outer diameter, and a distal portion wall thickness defined by the distal portion inner diameter and outer diameter, wherein the distal portion inner diameter is larger than the proximal portion inner diameter, and the outer diameter of the distal portion is substantially equal to the outer diameter of the proximal portion;
   a shoulder positioned between a cylindrical portion of the carrier tube proximal portion and a cylindrical portion of the carrier tube distal portion;
   at least one slit or slot formed in a distal-most edge of the distal portion, the slot extending in a proximal direction from the distal-most edge of the distal portion.

8. The carrier tube of claim 7, wherein the distal portion wall thickness is thinner than the proximal portion wall thickness.

9. The carrier tube of claim 8, wherein a transition from the carrier tube proximal portion to the carrier tube distal portion includes the carrier tube wall thickness gradually becoming thinner.

10. The carrier tube of claim 7, wherein the shoulder provides a transition from the carrier tube proximal portion to the carrier tube distal portion.

11. The carrier tube of claim 7, wherein a first edge of the at least one slit or slot overlaps a second edge of the at least one slit or slot.

12. A carrier tube, comprising:
    a proximal portion having an inner diameter, an outer diameter, and a proximal portion wall thickness defined by the proximal portion inner diameter and outer diameter, the proximal portion being affixed to a hub;
    a distal portion having an inner diameter, an outer diameter, and a distal portion wall thickness defined by the distal portion inner diameter and outer diameter, wherein the distal portion inner diameter is larger than the proximal portion inner diameter;
    a shoulder positioned between a cylindrical portion of the carrier tube proximal portion and a cylindrical portion of the carrier tube distal portion;
    a plurality of slits or slots proximally extending along the carrier tube from a distal edge of the distal portion; and
    at least one slit of the plurality of slits or slots, wherein a first edge of the at least one slit overlaps a second edge of the at least one slit.

13. The carrier tube of claim 12, wherein the distal portion outer diameter is substantially equal to the proximal portion outer diameter.

14. The carrier tube of claim 13, wherein the distal portion wall thickness is thinner than the proximal portion wall thickness.

15. The carrier tube of claim 14, wherein a transition from the carrier tube proximal portion to the carrier tube distal portion includes the shoulder.

16. The carrier tube of claim 14, wherein a transition from the carrier tube proximal portion to the carrier tube distal portion includes the carrier tube wall thickness gradually becoming thinner.

17. The carrier tube of claim 12, wherein at least one of the plurality of slits or slots extends to a distal end surface of the distal portion.

18. The carrier tube of claim 12, wherein the carrier tube is formed as a single, continuous tube.

19. The carrier tube of claim 12, wherein the plurality of slits have a length in the range of about 0.04 inch to about 1.8 inch.

20. The carrier tube of claim 12, wherein the plurality of slots have a length in the range of about 0.5 inch to about 1 inch.

* * * * *